(12) United States Patent
Magagnoli

(10) Patent No.: US 10,874,519 B2
(45) Date of Patent: *Dec. 29, 2020

(54) MODULAR SPACER DEVICE

(71) Applicant: Cossington Limited, Kingston upon Thames (GB)

(72) Inventor: Augusto Magagnoli, Cervia (IT)

( * ) Notice: Subject to any disclaimer, the term of this patent is extended or adjusted under 35 U.S.C. 154(b) by 103 days.

This patent is subject to a terminal disclaimer.

(21) Appl. No.: 16/092,242

(22) PCT Filed: Apr. 10, 2017

(86) PCT No.: PCT/IB2017/052063
§ 371 (c)(1),
(2) Date: Oct. 9, 2018

(87) PCT Pub. No.: WO2017/178957
PCT Pub. Date: Oct. 19, 2017

(65) Prior Publication Data
US 2019/0159905 A1    May 30, 2019

(30) Foreign Application Priority Data
Apr. 11, 2016    (IT) .................. 102016000036785

(51) Int. Cl.
*A61F 2/36*    (2006.01)
*A61F 2/30*    (2006.01)

(52) U.S. Cl.
CPC .......... *A61F 2/3609* (2013.01); *A61F 2/3662* (2013.01); *A61F 2002/305* (2013.01);
(Continued)

(58) Field of Classification Search
CPC .... A61F 2/4014; A61F 2/4612; A61F 2/4059; A61F 2/3609; A61F 2/4081; A61F 2/4609; A61F 2002/30538; A61F 2002/30649; A61F 2002/3625; A61F 2002/3822; A61F 2002/4011; A61F 2002/4051; A61F 2/30; A61F 2/40; A61F 2/4603; A61F 2/4607; A61F 2002/305; A61F 2002/30507; A61F 2002/30604; A61F 2002/365; A61F 2002/30593; A61F 2002/30607;
(Continued)

(56) References Cited

U.S. PATENT DOCUMENTS

2008/0234830 A1* 9/2008 Hershberger ......... A61F 2/3609
623/22.15
2011/0118848 A1* 5/2011 Faccioli ................ A61F 2/3662
623/22.11
(Continued)

FOREIGN PATENT DOCUMENTS

DE  102008030260 A1  12/2009
FR     2948012 A1   1/2011
(Continued)

*Primary Examiner* — Ann Schillinger
(74) *Attorney, Agent, or Firm* — Themis Law

(57) ABSTRACT

A modular spacer device implantable in the human body for the treatment of an infected articular seat includes a stem element, a head or ball element and coupling elements between the stem element and the head, wherein such coupling elements comprise a plurality of elongated teeth, placed at pre-established distances from each other, and a plurality of housing seats for the teeth.

25 Claims, 6 Drawing Sheets

(52) U.S. Cl.
CPC ............... *A61F 2002/3055* (2013.01); *A61F 2002/30331* (2013.01); *A61F 2002/30426* (2013.01); *A61F 2002/30448* (2013.01); *A61F 2002/30487* (2013.01); *A61F 2002/30672* (2013.01); *A61F 2002/30677* (2013.01); *A61F 2002/365* (2013.01)

(58) Field of Classification Search
CPC .... A61F 2002/3082; A61F 2002/30827; A61F 2/32; A61F 2/34
See application file for complete search history.

(56) References Cited

U.S. PATENT DOCUMENTS

| | | | |
|---|---|---|---|
| 2014/0222153 A1* | 8/2014 | Bonin, Jr. ............ | A61F 2/4637 623/18.11 |
| 2019/0159904 A1* | 5/2019 | Magagnoli ........... | A61F 2/3609 |

FOREIGN PATENT DOCUMENTS

| | | | |
|---|---|---|---|
| WO | 2006050106 A1 | 5/2006 | |
| WO | 2010015877 A1 | 2/2010 | |

* cited by examiner

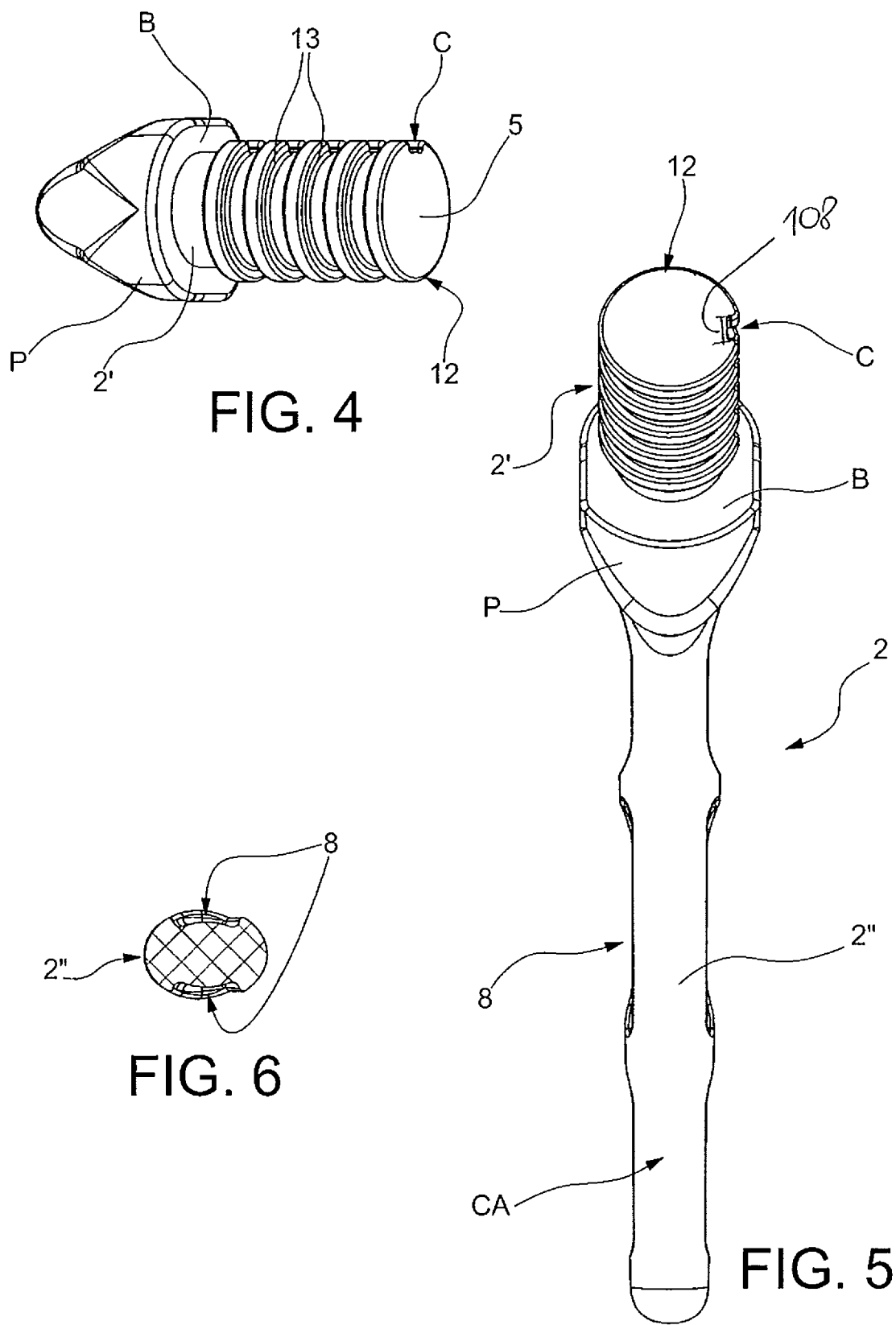

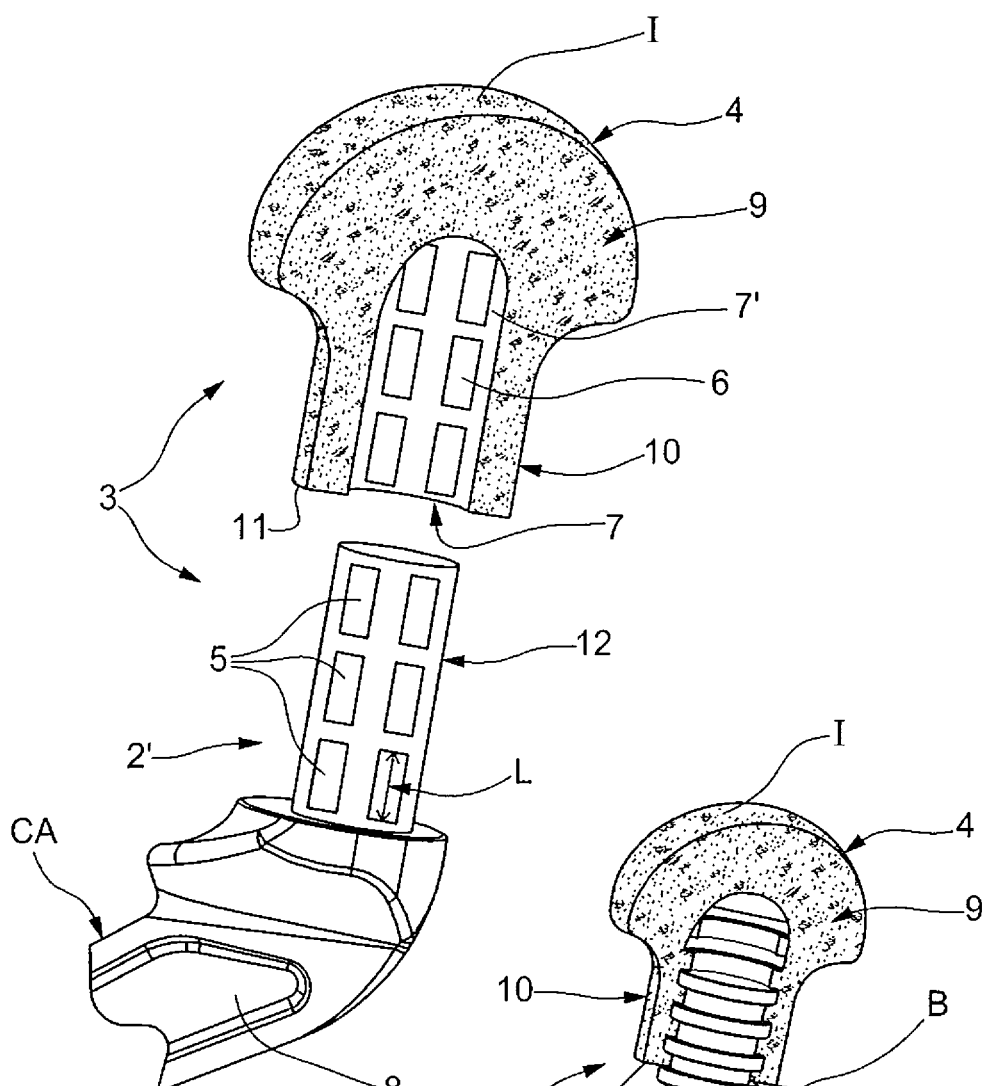
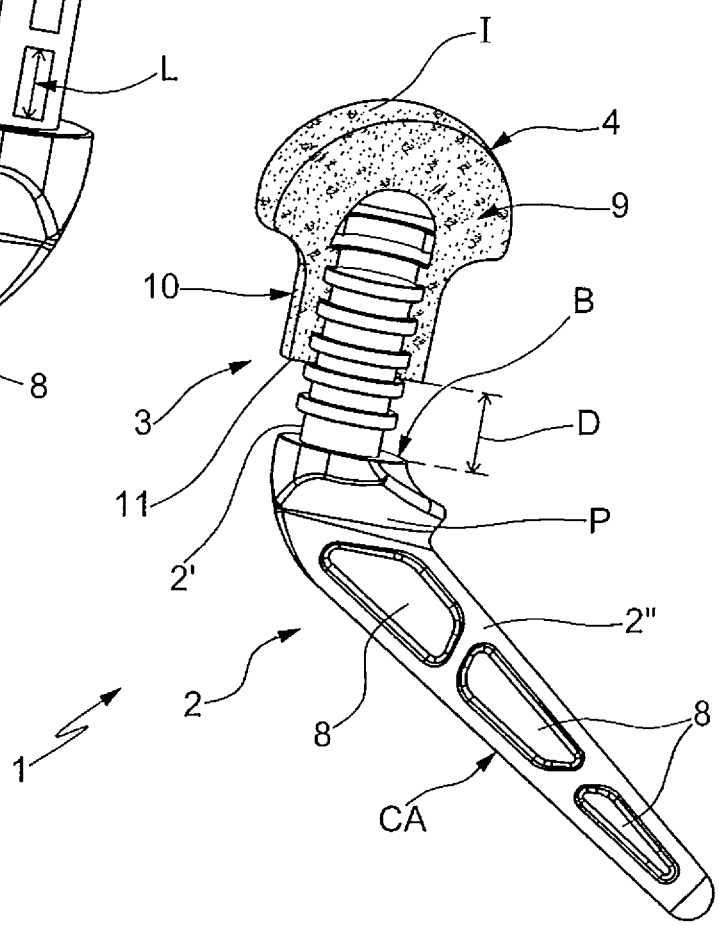
FIG. 7
FIG. 8

MODULAR SPACER DEVICE

TECHNICAL FIELD OF THE INVENTION

The present invention regards a modular spacer device for the treatment of an articular seat of the human body affected by infection, for example the hip or shoulder seat.

The present invention also regards a spacer device of temporary and disposable type, usable for the two-step treatment of prosthetic infections.

State of the Prior Art

It is known that joint prostheses can be colonized by bacteria and became infected.

In the cases of infection, the infected prosthesis is removed from the infection site and is substituted by an antibiotic spacer device, in order to defeat the infection from the implant site, maintaining substantially unaltered the shape of the bone seat or of the articular seat in which the new prosthesis will be subsequently implanted.

Due to the fact that the treatment of the infected seat occurs through the insertion of an antibiotic spacer and through the subsequent re-implanting of the new prosthesis, such procedure is known as "two-step treatment".

Spacer devices are known, for example for hip articulation, comprising a stem element, for the coupling with the upper femoral end, removably associable with a ball or head element, which can be associated with the acetabular cavity.

Such devices have an interchangeable and adjustable head on the stem element, in a manner so as to vary the distance of the head with respect to the stem itself.

The stem element has one end portion shaped substantially as a pin.

Such pin is housable inside the head of the spacer device and the distance between the neck of the stem component and the head can be adjusted based on the needs of the patient.

One example of a spacer device is described in the international application WO2010/015877.

The coupling mechanism between the head and the stem element can be of bayonet type, for example, especially in permanent prosthetic devices.

Nevertheless, this coupling type does not ensure high durability over time. Indeed, the components that determine the bayonet coupling usually having small size, are subjected to concentrated pressures and forces of size such to lead to the risk of breakage thereof.

In addition, such coupling mechanism is not easy to actuate, it is not quick to use, and this can lead to the prolongation of the implant times for a device equipped with such system.

In the case of a spacer device, since this is a temporary device, the need is felt, for the surgeon, to arrange a device capable of allowing a simple and quick adjustment of the head on the stem element, simultaneously ensuring good strength and durability over time of the device itself.

In addition, the known spacer devices are made of porous material, in a manner so as to comprise or be impregnated with one or more medical or pharmaceutical substances to be released in the human body, at the anatomical area where their implant is provided for.

The quantity of medical or pharmaceutical substance that can impregnate the spacer device is nevertheless limited, due in fact to the geometry and nature of the material constituting this type of device.

The surgeon must therefore arrange a spacer device capable of comprising or housing one or more medical or pharmaceutical substances in specific portions thereof, possibly independent of each other.

OBJECTS OF THE INVENTION

The task of the present invention is that of improving the state of the art.

In the scope of such technical task, one object of the present invention is to provide a spacer device, for the treatment of an infected seat of the human body, which is easy and quick to use.

A further object of the present invention is to provide a spacer device which can be adjusted by the surgeon, directly in the operating room, based on the anatomical characteristics of the patient.

Another object of the present invention is to provide a spacer device having a coupling mechanism, between head and stem, which is strong and has good durability over time.

A further object of the present invention is to provide a spacer device for the release of an amount of at least one medical or pharmaceutical substance in portions such to ensure the complete treatment of the infected seat, also possibly for long time periods.

In accordance with one aspect of the present invention, a spacer device is provided, according to claim 1.

The dependent claims refer to preferred and advantageous embodiments of the invention.

BRIEF DESCRIPTION OF THE DRAWINGS

Further characteristics and advantages of the present invention will be more evident from the detailed description of a preferred but not exclusive embodiment of a modular spacer device, illustrated by way of non-limiting example in the enclosed drawing tables in which:

FIG. 4 is a perspective view of a portion of a stem element of a modular spacer device according to the present invention;

FIG. 5 is a front view of the stem element pursuant to FIG. 2 according to another angle;

FIG. 6 is a section view taken along the plane VI-VI of FIG. 2;

FIG. 7 is a perspective view of a portion of a stem element and of a part of a head or ball element of a modular spacer device according to a further embodiment;

FIG. 8 is a perspective view of a modular spacer device according to a further version of the present invention;

EMBODIMENTS OF THE INVENTION

Figure 1:
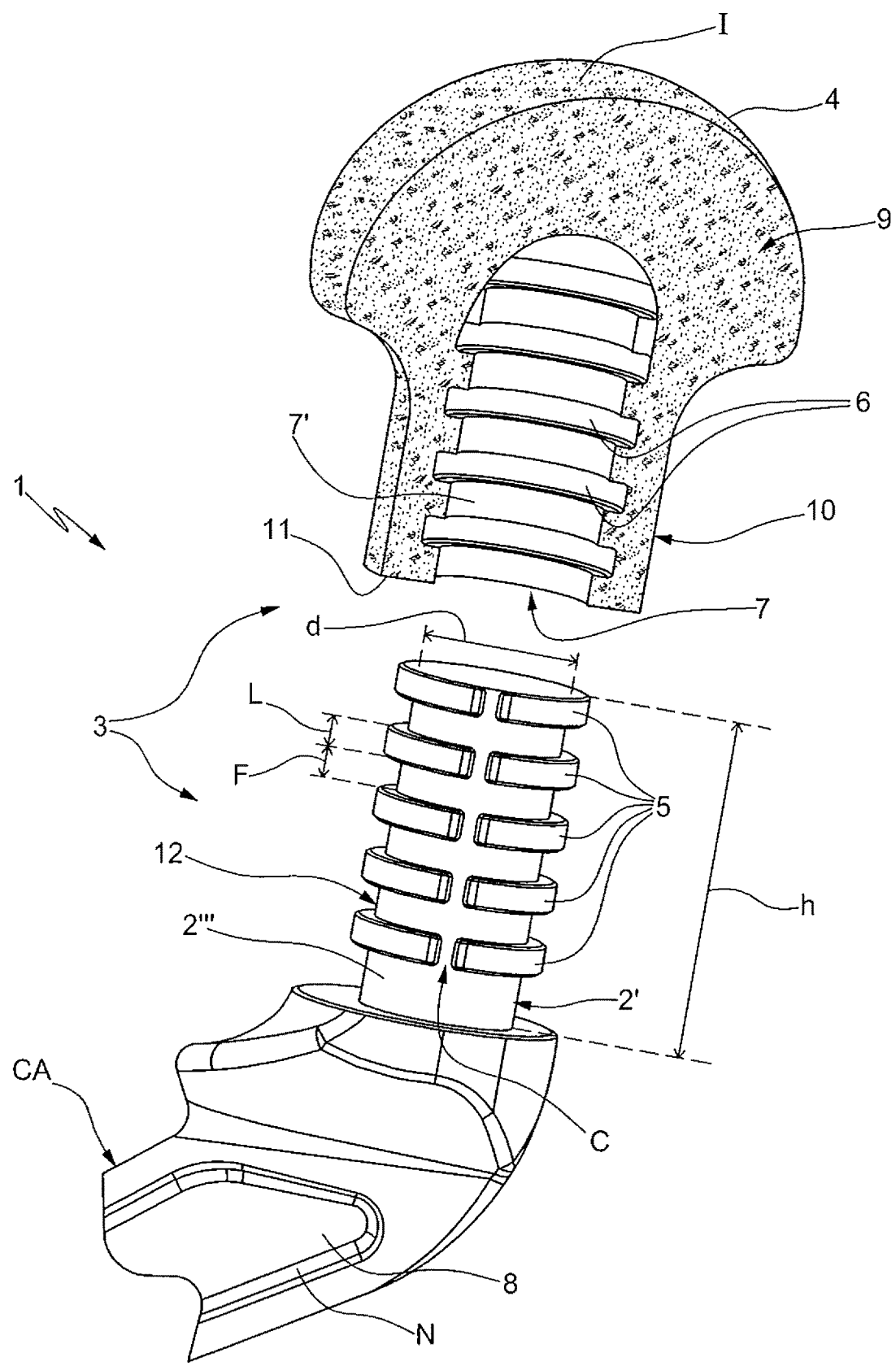
FIG. 1 is a perspective view of a portion of a stem element and of a partially sectioned head or ball element of a modular spacer device according to the present invention.

As is known, a spacer device 1 is provided for being implanted in a bone or articular seat of the human body, in substitution of an infected prosthesis and for the treatment of such articular seat before the re-implanting of a new prosthesis.

The spacer device 1 according to the present invention is of temporary and disposable type.

Indeed, such device carries out the treatment function as well as the function of maintenance of the shape of the bone or articular seat in which the new prosthesis is subsequently implanted.

With regard to the treatment function, such spacer device is adapted to treat an infection colonizing a bone or articular seat in which an infected prosthesis is housed, after the latter has been removed. Such function is carried out due to the release, by the spacer device, of one or more medical or pharmaceutical substances.

The spacer device 1 according to the present invention is of "modular" type since it can be assembled by the surgeon directly in the operating room and it can be adapted to the anatomical characteristics of the patient.

Hereinbelow, reference will be made to a modular spacer device 1 for the hip articulation. The spacer device 1 according to the present invention, nevertheless, can also be adapted to be implanted in a different bone seat, such as for example that relative to the shoulder articulation.

The modular spacer device 1 comprises a stem element 2, adapted to be coupled to a bone bed, and a head or ball element 4, adapted to be inserted in an articular area of the patient.

The spacer device 1 further comprises coupling means 3. The coupling means 3 are means for the mutual positioning between the stem element 2 and the head 4, as will be better described hereinbelow.

The stem element 2 and the head 4 are removably connected to each other.

The coupling means 3 are positioned between the stem element 2 and the head 4 and are adapted to removably connect or position the stem element 2 to the head 4.

The stem element 2 comprises at least one distal end 2' and an elongated body CA.

The elongated body CA has, in one version, a shape that is substantially conical or frustoconical or with pyramid frustum.

The elongated body CA has an external coupling surface 2", for coupling the spacer device 1 or at least one part thereof to the bone seat to be treated or to part thereof.

The coupling surface 2" is, therefore, shaped in a substantially complementary manner to the bone seat in which the stem element 2 is implanted.

During use, the coupling surface 2" is in contact with the bone tissue of the patient.

In such a manner, the correct positioning of the stem element 2 and the connection of the latter to the bone seat is facilitated.

With reference to the embodiment illustrated in the FIGS. 1-14, the coupling surface 2" is shaped in order to facilitate the coupling of the stem element 2 to the femoral end of the hip articulation.

In one version of the invention, the elongated body CA can comprise 4 faces, two substantially flattened faces and two substantially curved faces, one alternating with the other.

The two substantially flattened faces are positioned on opposite sides with respect to a plane S of longitudinal symmetry of the elongated body CA or of the stem element 2.

The two substantially curved faces are substantially perpendicular with respect to the plane S.

The stem element 2 comprises at least one recess 8.

In one version of such spacer device, it comprises a plurality of recesses 8 placed along the coupling surface 2" or at the same. In particular, the at least one recess 8 can be positioned along or at the flattened faces of the elongated body CA of the stem element 2.

The stem element 2 can comprise recesses 8 which are extended more or less deeply within it and/or positioned according to an arrangement that can vary as a function of the specific requirements.

In one version of the invention, the recesses 8 have a planar surface extension that is greater than the depth thereof.

In such a manner, due to this specific shape, it is possible to completely fill each recess 8 without running the risk that some parts thereof accidentally lack filling material. There is a risk of this happening, for example, when the recesses have greater depth than width or when the opening that they determine on the surface of the medical device is limited. Indeed, in these cases, air bubbles could for example remain trapped within the recess and this could prevent the correct filling of the latter.

The at least one recess 8 in fact forms a seat for housing a filling material comprising, in one version of the invention, at least one medical or pharmaceutical substance in the stem element 2 of the spacer device 1.

Hence in accordance with the gravity of the infection present, all the recesses can be filled or only some of these can be filled with the filling material comprising the at least one medical or pharmaceutical substance and/or different pharmaceutical substances can be housed in the various recesses, depending on the mode of expansion of the infection in the articular seat in question.

The recesses 8, in practice, act as seats for the storage of at least one medical or pharmaceutical substance to be released within the infected seat to be treated.

Such filling material, which contains the at least one medical or pharmaceutical substance, can be of hardening or solidifiable type.

In one version of the invention, the filling material can be prepared by the surgeon during the operating procedure.

Such filling material can lack medical or pharmaceutical substances and can be admixed therewith based on the selection of the surgeon and on the needs of the patient.

In a further version of the invention, the aforesaid filling material can comprise at least one medical or pharmaceutical substance previously arranged in the material that constitutes the filling material itself, and may possibly, during preparation, be admixed with a further substance.

In addition, by virtue of the step of preparation and solidification to which it is subjected, the filling material can be porous.

The filling material, in one version of the invention, is a bone cement, a polymethylmethacrylate-based bone cement, or polymethylmethacrylate or a ceramic material. The overall volume of the recesses 8 or of the recess 8 is thus adapted for the time period estimated for treating the infection underway in the seat in which the spacer device is placed.

The filling material is a biologically compatible material.

The size of the pores possibly present in the filling material or in the spacer device 1 is such to prevent new bone growth during use within the same and, hence, within the spacer device, which as stated is temporary.

One such configuration of the pores, therefore, facilitates the subsequent removal of the spacer device itself from the treated bone or articular seat, once its treatment function is completed.

By way of example, the pores can have, in one version, dimensions on average smaller than 100 micron.

In such a manner, the pores present in the filling material and/or in the spacer device carry out a capillary function. The relative material, therefore, due to such capillarity, ensured by the size of the pores, can absorb at least one medical or pharmaceutical substance (present for example in liquid or solution form), maintain it at its interior and gradually release it over time.

In a further version of the invention, at least some of the recesses 8, in accordance with the specific needs, can be filled or house the filling material lacking medical or pharmaceutical substances.

If there is a plurality of recesses 8 along the coupling surface 2", one obtains a structure with open cells side-by-side each other.

For example, each recess can have an external surface corresponding to ½ to ¼ or even ⅙ to ⅛ of the surface of the face or of the surface on which it is present, for example of the faces of the elongated body CA of the stem element 2.

As stated, the recesses 8 are flat and positioned at the interface with the bone tissue, in a particular manner, for example, for the stem element 2.

In one version of the invention, the filling material is a fluid and/or pasty mass, obtained by joining with bone cement one or more pharmaceutical or medical substances, such as one or more antibiotics, for example.

In such a manner, in the version in which the filling material M comprises bone cement and the material with which the spacer device is made is bone cement, the fluid bone cement of the filling material melts with the bone cement of the spacer device, making a perfect joining between the same. In such a manner, there is no risk, for the patient, that the filling material will be detached from the respective spacer device, once the latter is implanted in the human body.

In addition, the flat profile of the recesses 8, as well as the presence of the ribs N, which are short continuous sections, allows a facilitated filling of the recesses themselves with the filling material. In such a manner, as stated, one is able to easily level the latter with the external surface of the spacer device or with the external surface of the ribs N, for example due to the aid of a simple spatula. Such alignment is important for avoiding possible over-thicknesses or discontinuities of fresh cement added by the doctor, with the consequent impossibility of inserting the spacer device in the proper cavity or bone seat, such as the diaphyseal canal for the stem element 2.

A further aspect of at least one version of the present invention is that the spacer device 1 carries out the mechanical function required for its use. Therefore, the material that constitutes it must be able to support the loads applied by the patient. Such aspect however does not regard the filling material, whose object is not structural or mechanical but rather only that of vehicle for the at least one medical or pharmaceutical substance.

Consequently, the filling material can comprise, in one version of the invention, more antibiotic than what would be possible to insert in the material of the spacer device, indeed because—unlike the latter—it does not have to exert mechanical strength.

In a still further version, a medical or pharmaceutical substance, such as at least one antibiotic can be present or admixable with the material that constitutes the spacer device. In such version, such material is porous. Possibly, this is bone cement or PMMA-based bone cement. If the teeth 5 and the seats 6, 6A are made of the same material, these are also porous and provided or admixable with such at least one medical or pharmaceutical substance.

The recesses 8, as stated, are separated from each other by ribs N interposed between the recesses 8 themselves: such ribs N are adapted to ensure a division between the recesses 8, in a manner such that the medical or pharmaceutical substances contained in the different recesses 8 do not come into contact with each other.

In one version of the invention, the ribs N are continuous and substantially rectilinear sections.

In addition, such ribs N can be adapted to improve the coupling of the coupling surface 2" to the bone seat to be treated, and/or to act as reinforcement element for the stem element 2 itself.

Such ribs N, in one version of the invention, can be made of different material than that which constitutes the stem element 2.

Figure 2:
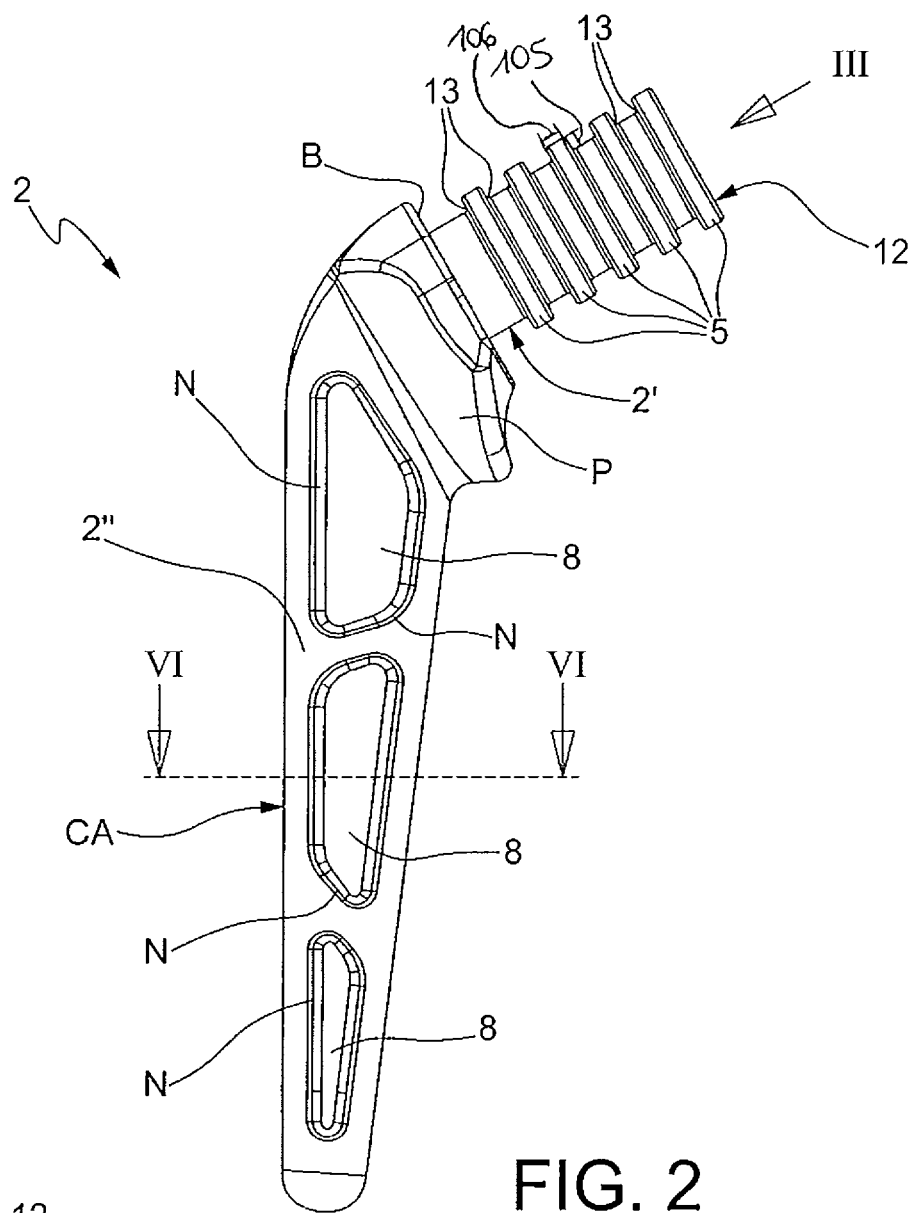
FIG. 2 is a side view of a stem element of a modular spacer device according to the present invention.
Figure 3:
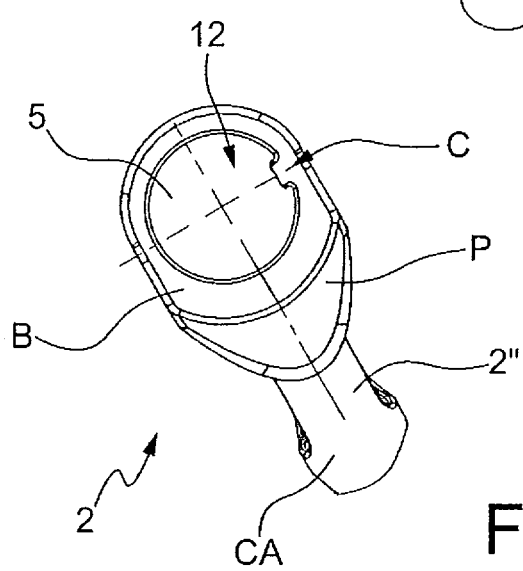
FIG. 3 is a top view along the direction III of the stem element of FIG. 2.
Figure 11:
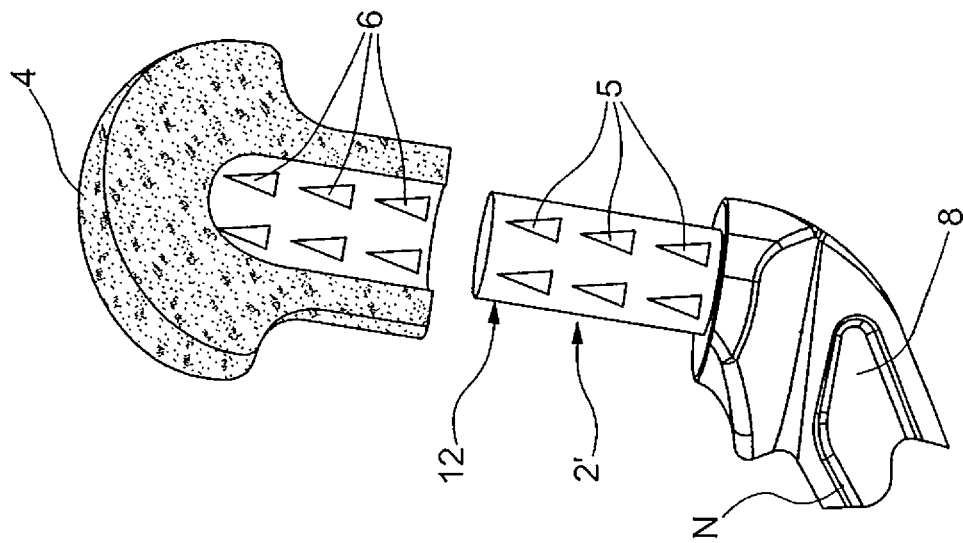
FIG. 11 is a perspective view of a portion of a stem element and of a part of a head or ball element of a modular spacer device according to a further embodiment.
Figure 10:
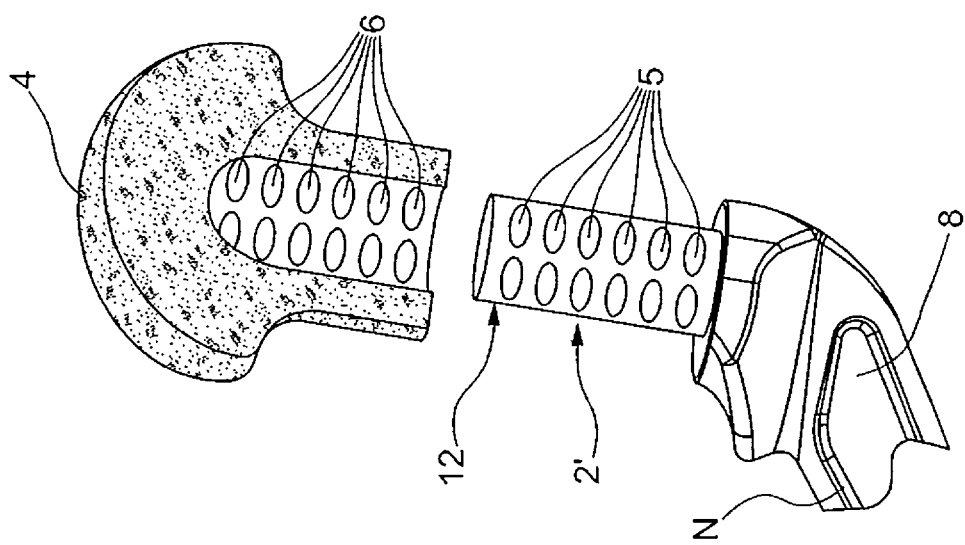
FIG. 10 is a perspective view of a portion of a stem element and of a part of a head or ball element of a modular spacer device according to a further embodiment.
Figure 9:
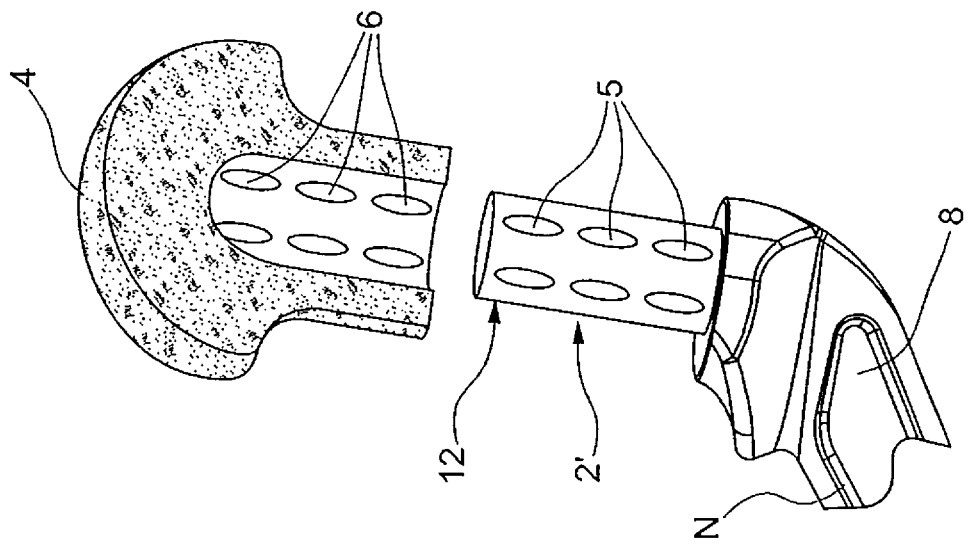
FIG. 9 is a perspective view of a portion of a stem element and of a part of a head or ball element of a modular spacer device according to a further embodiment.

In one version of the invention, illustrated for example in FIG. 2, each flattened face of the elongated body CA or at least one lateral portion thereof is affected by three recesses 8, separated by ribs N.

In particular, the ribs N can have a tilted progression, opposite with respect to the adjacent rib. For example, a first rib N, placed for example at the distal end or portion 2' of the stem element 2, substantially has the same progression as a third rib N (which separates a second recess 8 from a third recess 8) while a second rib N (which separates a first recess 8 from the second recess 8) will have opposite progression, and so forth. Each rib N is interposed between the recesses 8.

The thickness of the ribs N is smaller than the size (i.e. respect to both the length and width) of each recess 8. The thickness of the ribs N is that size which is extended perpendicular to the greater size or extension thereof, the latter also termed length of the rib.

The depth of the ribs N corresponds with that of the adjacent recesses 8.

The stem element 2 can be made of biologically compatible material, possibly porous, for example made of polymethylmethacrylate (PMMA), polyvinylchloride (PVC), polystyrene (PS), polyethylene (PE), ultra-high molecular weight polyethylene (UHMWPE), high or low density polyethylene, etcetera or a bone cement or non-polymer materials, ceramics, metals, metal alloys, metal-organic compounds, and/or a combination thereof.

In one version of the present invention, the biologically compatible material is a polymethylmethacrylate (PMMA) based bone cement.

In one version of the invention, the spacer device can have a metal core and a bone cement—based external coating. In the case of the recesses 8, these in such version are made in the bone cement layer, so that no metal portion of the spacer device 1 is exposed.

The aforesaid biologically compatible material can comprise at least one medical or pharmaceutical substance or it can initially lack medical or pharmaceutical substances. According to a further version of the present invention, the biologically compatible material can be a ceramic cement, such as calcium sulfate known as plaster or $CaSO_4$, which in addition to solidifying in limited times is able to release calcium ions.

In order to make the stem element 2, further materials of biocompatible type can also be used, with respect to that described above, without departing from the protective scope of the present invention.

In one version of the invention, the biocompatible material is of permanent type, i.e. it cannot be dissolved or degraded inside the human body.

The ribs N can be made of biologically compatible and porous material, so as to be impregnated, in one version, with medical or pharmaceutical substances to be released in the infected bone seat.

The distal end 2' of the stem element 2 comprises a shank 12 or is shaped as a shank 12. Such shank 12 is adapted to be coupled with the head 4.

Such shank 12 is connected to the body CA of the stem element 2 at a flat base B of the latter.

The stem element 2 can comprise a portion P, at the distal end 2'. Such portion P is elongated and/or tapered and/or enlarged proceeding from the body CA of the stem element 2 towards the flat surface B, from which the shank 12 departs.

The portion P comprises a first end connected to the body CA and a second end constituted by the flat base B.

The flat base B, as stated, is fixed to the shank 12.

In one version of the invention, the body CA, the portion P and the shank 12 are made of a single piece. In such case, the stem element 2 is made of a single piece.

In this version, also the coupling means 3—or at least one component thereof—can be made of a single piece with the stem element 2. Such aspect will be described in detail hereinbelow.

According to the version illustrated in FIGS. 1-14, such shank 12 can appear in the form of a cylinder with height h and diameter d, having base area smaller than that of the flat base B on which such shank 12 is fixed or from which it departs.

According to one embodiment, the cylindrical shank can have height h equal to 35 mm and diameter equal to 16 mm.

In addition, the aforesaid shank 12 comprises a lateral surface 2''' which can be smooth and/or rough.

The shank 12 can have different geometric forms, though always adapted to ensure the function of coupling between stem element 2 and head 4.

In one version of the invention, therefore, the shank 12 can for example have the form of a right prism or of another geometric solid.

According to the illustrated embodiment, the head or ball element 4 can comprise at least one substantially hemispherical cap 9.

In one version of the invention, the head component 4 further comprises a projecting portion 10 which during use is extended towards the distal end 2' of the stem element 2.

The projecting portion 10 is substantially annular.

The projecting portion 10 departs from the substantially hemispherical cap 9 or from a base thereof, conferring a substantially "mushroom" shape to the head element 4.

In one version of the invention, the projecting portion 10 and the substantially hemispherical cap 9 of the head or ball element 4 are made of a single piece.

In a further version of the invention, such element has a substantially spherical shape. According to a further non-illustrated version, the head component 4 can only comprise a substantially hemispherical cap 9.

The head or ball element 4 and/or the substantially hemispherical cap 9 and/or, if present, the projecting portion 10 comprise an external surface I, placed in contact with or directed during use towards the bone tissue.

Such external surface I, in a non-illustrated version of the invention, can comprise at least one recess, having characteristics analogous to those of the at least one previously-described recess 8 present in the coupling surface 2'' of the stem element 2.

Also such at least one recess 8 can contain a filling material containing or not containing at least one medical or pharmaceutical substance.

It is possible to arrange at least two ball or head elements 4 and/or substantially hemispherical caps 9 having different diameters, in a manner such that the surgeon can select the size of such component that is best adapted to the anatomical characteristics of the single patient.

Analogously, it is possible to arrange at least two stem elements 2 having different sizes, in a manner such that the surgeon can select the size of such component that is best adapted to the anatomical characteristics of the single patient.

The present invention, therefore, can also be directed towards a kit comprising at least one pair of components of different size, in a manner such that the surgeon can select the size most adapted to the specific needs.

The head or ball element 4 comprises a cavity or hole 7 for housing the shank 12 of the stem element 2.

The cavity 7 comprises a lateral surface 7'. The surface 7' is internal.

In addition, the cavity 7 comprises a hole for the entrance of the shank 12 in the head or ball element 4.

The entrance hole is delimited by a base surface 11, which is a surface that connects the external surface I to the lateral surface 7' of the head or ball element 4.

The cavity 7 of the head 4 has configuration substantially corresponding to that of the shank 12 of the stem element 2, in a manner such that the shank 12 can be inserted at least partially in the cavity 7, thus causing the coupling and adjustment of the position of the stem element 2 and of the head or ball element 4.

Therefore, when the shank 12 has the shape of a cylinder, the cavity 7 has the shape of a dome with cylindrical base, with height and diameter slightly greater than or equal to those of the shank 12 and/or of the diameter d and height h of the shank 12 itself.

Indeed, the dimensions of the cavity 7 must be such to allow the insertion and coupling with the shank 12.

The coupling means 3, as also stated above, are adapted to ensure a coupling between the head or ball element 4 and the stem element 2 and, more precisely, between the cavity 7 of the head and the shank 12. In particular, the coupling means 3 allow stabilizing, possibly in a temporary manner, a specific position of the shank 12 with respect to the cavity 7, i.e. the distance of the stem element 2 with respect to the head or ball element 4. As will be better described hereinbelow, such positioning is then stably and definitively fixed by means of a fixing material. In such a manner, the spacer device according to the present invention, having a certain position ensured by the coupling means 3, and a certain stability and a certain fixing of its components, given by the fixing material, will be adapted to support the required loads.

Such coupling means 3 allow an adjustment of the size of the spacer device 1 based on the anatomy of the patient. More in detail, such adjustment consists of varying the distance D (for example represented in FIG. 8) between the head or ball element 4 and the stem element 2.

Such coupling means 3 therefore allow varying or adjusting the distance D between the flat base B of the stem element 2 and the base surface 11 of the head or ball element 4.

The coupling means 3, in one version of the invention, comprise at least one tooth 5 or a plurality of teeth 5 and at least one seat 6 or a plurality of seats 6, in which said one or more teeth 5 are adapted to be housed.

By varying the housing position of the teeth 5 in the seats 6, it is possible to vary the aforesaid distance D.

In one possible configuration, the teeth are placed on the lateral surface 2''' of the shank 12 and the seats 6 are made in the cavity 7 of the head 4, at the lateral surface 7' thereof. In a further configuration, not illustrated, the teeth 5 are placed on the lateral surface 7', and are projecting with respect thereto, for example projecting towards the interior of the head 4, while the seats 6 are made in the shank 12, at its lateral surface 2'''.

The teeth 5 comprise portions, possibly elongated, and projecting with respect to the surface on which they are positioned, i.e. with respect to the lateral surface 2''' of the shank 12 or with respect to the lateral surface 7' of the cavity 7 comprised in the head 4. In at least one version of the invention, the teeth 5 have elongated extension according to one direction parallel to the longitudinal axis or to the longitudinal symmetry axis of the shank 12 and/or of the head 4.

In an alternative version, the teeth 5 have elongated extension according to a direction perpendicular to the longitudinal axis or to the longitudinal symmetry axis of the shank 12 and/or of the head 4.

In one version of the invention, the teeth 5 are placed parallel and at pre-established distances F from each other, in a manner such that the surgeon can decide the distance D for adjusting the spacer device 1 in the operating room. Indeed, by knowing the measure of the pre-established distances F between the various teeth 5, the surgeon decides in which seats 6 to house the various teeth 5, so as to define the desired distance D based on the anatomical characteristics of the single patient.

In the version illustrated in FIGS. 1-5 and 8, the teeth 5 are parallel to each other and have an annular shape.

In such version, the teeth 5 are placed around the shank 12, coaxial with the latter and projecting with respect to its lateral surface 2'''; the seats 6 are corresponding annular cavities or grooves, made at the lateral surface 7' of the cavity 7 of the head or ball element 4.

In an alternative version, the teeth are rings parallel to each other, placed at the lateral surface 7' of the cavity 7 and projecting with respect thereto, while the seats 6 are corresponding annular cavities made in the lateral surface 2''' of the shank 12.

In a further version, as illustrated in the FIGS. 7 and 9-11, the teeth 5 are projecting portions, projecting with respect to the surface on which they rest or from which they depart, of rectangular, oval, triangular or other elongated form, distributed in rows or to columns which are extended along the surface itself to which they are fixed or from which they depart. In such case, the seats 6 have shape and position complementary to that of the teeth 5, so as to ensure a coupling between head 4 and stem element 2.

Therefore, the teeth 5 and the respective seats 6 have, in such version, a substantially geometric solid shape, such as a prism or a cylinder.

Such geometric solid comprises two bases, one of which is fixed or made in the lateral surface 2''' of the shank 12 or in the lateral surface 7' of the cavity 7, in which such bases have a polygonal or circular shape.

Such teeth 5 can comprise, in at least one version of the invention, trimming 13 (for example illustrated in FIGS. 2 and 4 but also applicable to the other embodiments or versions of the present invention) adapted to improve and render more stable the coupling of the teeth 5 within the seats 6.

Such trimming 13 can be made of different material with respect to that which constitutes the teeth 5.

In addition, the trimming 13 can be made of a flexible and moldable material, adapted to fix the teeth 5 within the respective seats 6 and/or to allow the entrance thereof in the seats 6 themselves.

For example, such trimming 13 can be made of a deformable material or of PVC or of rubber.

The teeth 5 have a width L along the direction defined by the height h or along a longitudinal direction of the shank 12.

In one version of the present invention, the teeth 5 have width L equal to 3 mm and/or project 2 mm with respect to the surface on which they are placed.

The teeth 5 can be made of the same material as the stem element 2 and/or as the head or ball element 4 and/or they can be made in a single piece therewith.

The teeth 5 can be made of biocompatible material, such as polymethylmethacrylate (PMMA), polyvinylchloride (PVC), polystyrene (PS), polyethylene (PE), ultra-high molecular weight polyethylene (UHMWPE), high or low density polyethylene, etcetera or a bone cement or non-polymer materials, ceramics, metals, metal alloys, metal-organic compounds, and/or a combination thereof.

In the embodiment illustrated in the figures, the teeth 5 and the seats 6 constitute a coupling mechanism of snap type.

In one version of the invention, when the coupling occurs as a snap, a material with elastic properties can be present in the at least one tooth 5 and/or in the at least one seat 6 and/or in the stem element 2 and/or in the head or ball element 4, such elastic material adapted to be at least slightly deformed in order to allow the fitting of the at least one tooth 5 in the at least one seat 6, without creating cracks or damaging the material constituting the stem element 2 or the head or ball element 4.

In the version of the invention illustrated for example in FIG. 1, the teeth 5 appear in the form of open rings, having at least one opening C along each tooth 5.

The opening C is a kind of recess with respect to the outermost surface of the annular teeth 5.

According to one embodiment, also the opening C can assist in the snap coupling between the teeth 5 and the seats 6, since it can allow an elastic deformation of the teeth 5 when they are forced to penetrate inside the seats 6.

Such openings C can be positioned on the teeth 5 so as to be parallel to each other, so as to create a channel free of projections on the surface on which such teeth are placed. In such a manner, the openings C are positioned along a same axis, parallel to the longitudinal axis of the shank 12. In a further version, the openings C can be positioned in an offset manner, i.e. not aligned along a same axis parallel to the longitudinal axis of the shank 12.

In such version, the seats 6 can have annular shape that is corresponding but recessing with respect to the lateral surface 7' of the cavity 7.

In an alternative version, the teeth 5 are placed parallel to each other and the space between the teeth 5, corresponding to the pre-established distance F of separation therebetween, constitutes at least one seat 6A. In such version, the teeth 5 appear in the form of open rings, having at least one opening C along each tooth 5.

The opening C is a kind of recess with respect to the outermost surface of the annular teeth 5.

In such case, the cavity 7 can have a diameter or a surface slightly greater than or equal to that given by the sum of the measure of the diameter d of the shank 12 and of the measure corresponding to the projection 105 of each tooth 5.

In addition and/or as an alternative, the cavity 7 can have a projection 5A, with corresponding dimensions, at least regarding width, with respect to the dimensions of the opening C of the teeth 5.

In particular, the projection 5A has a height F or slightly smaller than F and a width 107 corresponding to the width of the opening C or slightly smaller than the same.

During the step of insertion of the shank 12 inside the cavity 7, therefore, the projection 5A, having suitable size, can pass along the channel determined by the opening C of each tooth 5. When the surgeon has established the correct distance D between the stem element 2 and head or ball element 4, it is possible to rotate the stem element 2 with respect to the head or ball element 4 (or vice versa), in a manner so to allow the sliding of the projection 5A in the seat 6A formed by the space between one tooth 5 and the next.

It is necessary therefore that the projection 5A have a height (calculated along a direction parallel to the longitudinal axis of the shank 12) equal to or smaller than the distance F between one tooth and the next. If the teeth 5 have such shape, the seats 6 can be shaped as, and/or the cavity 7 can have, one or more projecting portions 5A adapted to be introduced in the spaces present between one tooth and the next, possibly through the openings C, so as to obtain a coupling between the stem element 2 and the head or ball element 4.

In a particular version of the invention, at least two projections 5A can be present. In such case, the projections 5A are aligned along a same longitudinal axis, parallel to the longitudinal axis of the shank 12 and/or to the longitudinal axis of the cavity 7. In such case, also the openings C are aligned along an axis parallel to the longitudinal axis of the shank 12 and/or to the longitudinal axis of the cavity 7. In such version, the projections 5A are positioned, with respect to each other, spaced by a distance equal to or slightly greater than the width L of the teeth 5, such that they can be inserted in two adjacent seats 6A (which are separated, along a longitudinal direction parallel to the longitudinal axis of the shank 12, by a measure equal to the width L of the teeth 5).

In one version of the invention, therefore, the coupling means 3 comprise bayonet coupling means. The configuration of the modular spacer device 1, according to the present invention, allows a considerable increase of strength and durability of the coupling means between head and stem. Indeed, such coupling means comprise teeth which can have greater size than that of known devices, possibly prosthetic, and consequently the pressures and forces to which such teeth are subjected are divided over large areas, ensuring a smaller probability of breakage thereof over time.

As is visible for example in FIG. 2 (and also valid for other versions of the invention), considering the teeth 5 for the extension thereof away from the lateral surface 2''' of the shank 12, the teeth 5 have a section—taken along the longitudinal symmetry plane of the stem element 2—having a substantially rectangular or quadrangular shape. In particular, each tooth 5 projects a distance 105 from the lateral surface 2''' of the shank 12. In addition, each tooth has a height 106 (or width L), considered along the longitudinal direction of the shank 12.

In one version of the invention, the height 106 can vary from tooth to tooth.

In a further version, the teeth 5 can have a semicircular or triangular section and/or a section with rounded edges.

In one version of the invention, nevertheless, the rectangular or quadrangular section confers a greater stability of connection or attachment with the head or ball element 4. Naturally, the possible housing seats 6 for the teeth 5 have shape corresponding to that of the teeth 5 themselves.

In addition, in at least one version of the invention, approximately 3 to 7 teeth 5 are present, preferably 5, positioned starting from the top portion of the shank 21 to the area thereof closest to the base B of the stem element 2.

In addition, the teeth can be present in a number of rows ranging from 3 to 7, preferably 5 rows.

The same number of possible seats 6 and teeth 5 can be present, or there is the same number of rows of the teeth 5.

Figure 12:
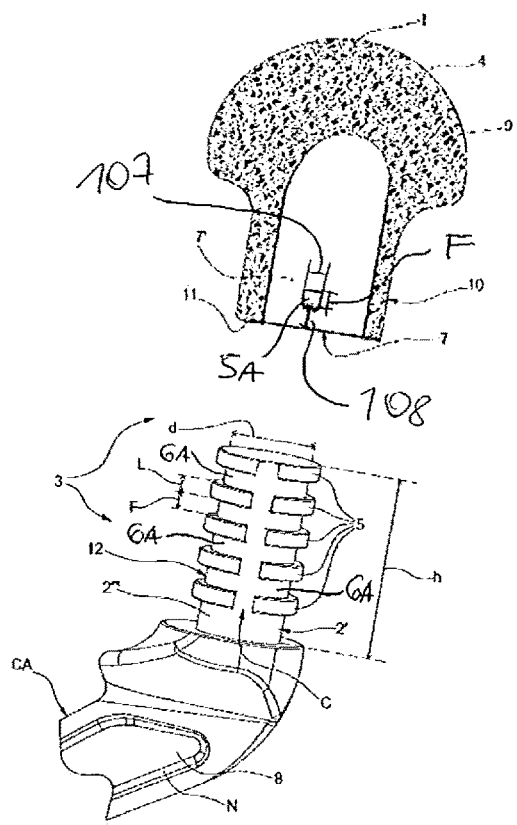
FIG. 12 is a side view of one version of the modular spacer device according to the present invention.
Figure 13:
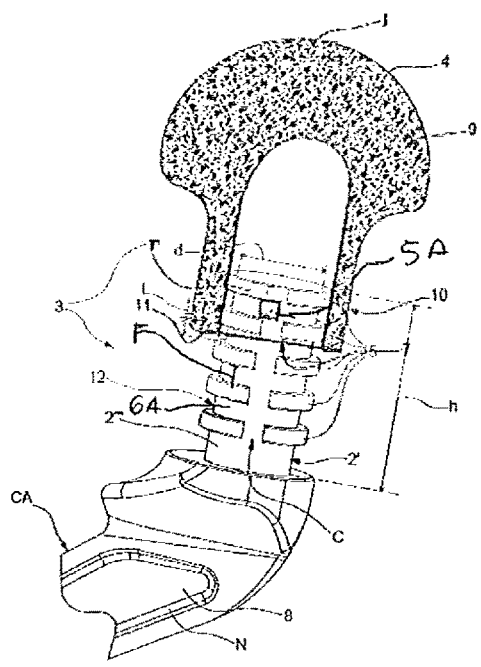
FIG. 13 is a view of the version of FIG. 12, in which the two elements that constitute the spacer device are situated assembled to each other at the maximum distance.
Figure 14:
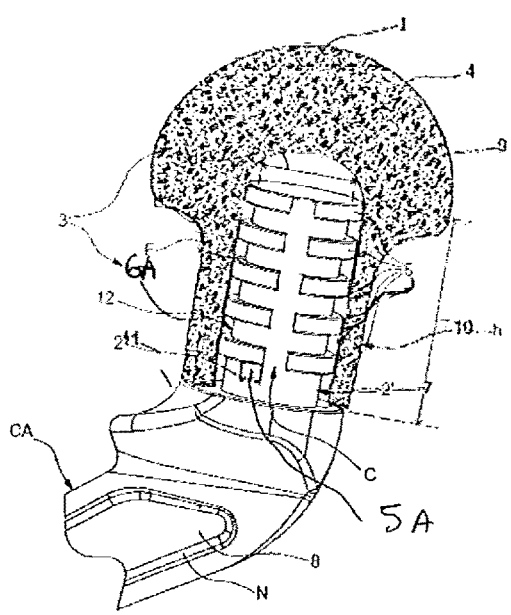
FIG. 14 is a view of the version of FIG. 12, in which the two elements that constitute the spacer device are situated assembled to each other at the minimum distance.

The projection 5A, in the version illustrated in FIGS. 12 to 14, is placed at a distance 108 from the surface 11 of the head or ball element 4. In particular, the lower surface of the projection 5A is situated at the distance 108 from the surface 11.

The projection 5A, therefore, is positioned at the zone of the head or ball element 4 closest to the opening delimited by the surface 11.

In the version in which the projection 5A is positioned on the lateral surface 2''' of the shank 12 and the teeth 5 and the seats 6A are positioned on the internal surface of the cavity 7, the projection 5A will be situated at a distance 108 from the apical portion of the shank 12, or at least in the zone closest to the apical portion of the shank 12 itself. In such a manner, the openings C themselves would be positioned in the teeth 5 of the head 4. In such a manner, it is possible to couple the stem element 2 and head or ball element 4 at a maximum distance D, such to in any case allow a stable coupling, in which the projection 5A is housed in the seat 6A closest to the apical part of the shank 12, as is visible in FIG. 13.

In addition, it is possible to couple stem element 2 and head or ball element 4 at a minimum distance D, in which the projection 5A is housed in the seat 6A closest to the base B of the stem element 2, as is visible in FIG. 14. In such position, the distance D can be zero and the base B can be in contact with the surface 11 of the head or ball element 4.

Naturally, all intermediate positions are possible between the maximum distance D and the minimum distance, in a discrete manner in accordance with the number of seats 6A or seats 6 present, in a manner so as to meet the anatomical needs of the patient.

In a still further version of the present invention, not illustrated in the figures, in addition to the teeth 5, seats 6A and projection 5A, further seats 6 could be present, for housing the teeth 5. In such a manner, the coupling means 3 could be both snap coupling and bayonet coupling.

The projection 5A has a section corresponding to that of the seats 6A in which it is inserted, for example, in the version in which the teeth 5 have rectangular or quadrangular section, the seats 6A have rectangular or quadrangular section and analogously also the projection 5A has such shape or rectangular or quadrangular section.

The coupling means 3 therefore include at least one tooth 5, at least one projection 5A and/or at least one seat 6, 6A.

The teeth 5, in any case, determine the relative position between neck and head of the spacer device 1 according to the present invention. However, the teeth 5 do not determine the definitive fixing between the parts, a fixing which is determined by the presence of a fixing material or glue means or final fixing means, which is capable of rendering the position defined by means of the teeth 5, or generally the coupling means 3, permanent.

Indeed, once the components constituting the spacer device 1 are assembled, such assembly is definitively fixed through a fixing material, such as bone cement, glue material, monomers or other, possibly allowing an at least surface melting of the material constituting such components and obtaining a sort of single body.

Therefore, the fixing material can be of a different nature. For example, acrylic bone cement can be used, or a cyanacrylic glue, or an organic solvent, or a mixture of multiple components, such as chloroform, methylmethacrylate, ethyl acetate, dichloromethane and not only or at least one of the same. Of course, whatever glue means is used, it must be stable and biocompatible.

The fixing material, once inserted, penetrates between the seats or channels of the coupling means 3 and locks in position the stem element 2 with the head or ball element 4, in a manner such that it is no longer possible to rotate one with respect to the other, nor modify the distance thereof. In such a manner, a stable fixing or coupling is created, so as to render the spacer device adapted for being implanted.

In such a manner, a stable and safe coupling is ensured between the two elements of the spacer device 1.

According to one version, the fixing material is inserted or poured in the cavity or hole 7 of the head or ball element 4. Subsequently, the shank 12 of the stem element 2 is inserted within the cavity or hole 7. In such a manner, the fixing material will completely cover the surfaces of the shank 12 and/or of the cavity 7, and/or will fill possible empty spaces thereof, as well as possibly the 6, 6A.

In such a manner, a mechanically solid and consolidated fixing is obtained between the two components of the device 1.

The object of the present invention is also a method for the assembly of the device 1 according to the present invention. Such method provides for supplying a spacer device 1 comprising a head or ball element 4 and a stem element 2 equipped with a shank 12. The head or ball element 4 comprises a cavity or hole 7 for housing the shank 12 of the stem element 2.

The method therefore provides for at least partially inserting the shank 12 in the cavity 7.

In such a manner, one determines the coupling and adjusting of the position of the stem element 2 and of the head or ball element 4.

In particular, the method also provides for a step of supplying coupling means 3, adapted to ensure a coupling between the head or ball element 4 and the stem element 2 and, more precisely, between the cavity 7 of the head and the shank 12.

In one version of the invention, the coupling means 3 are made of a single piece respectively with the stem component 2 or with the head or ball element 4.

As is inferred from the preceding description, in order to establish such adjustable connection between stem element 2 and head or ball element 4, it would be possible to have only one tooth 5 and a plurality of seats 6 or a projection 5A and a plurality of seats 6A between the teeth 5 having open annular shape.

Nevertheless, at least in one version of the invention, when multiple teeth 5 are inserted and/or connected in multiple seats 6, a greater coupling stability is achieved and there is a smaller risk of having an accidental disconnection between the two components.

The method then provides for supplying coupling means 3 comprising at least one tooth 5 or a plurality of teeth 5 and/or at least one projection 5A and at least one seat 6, 6A or a plurality of seats 6, 6A in which said one or more teeth 5 and/or such at least one projection 5A are adapted to be housed.

The method then provides for inserting one or more teeth 5 in one or more seats 6 in a manner so as to removably connect the stem element 2 or the shank 12 with the head or ball element 4, or with its cavity 7. The insertion of one or more teeth 5 in one or more seats 6 can determine a snap coupling.

Such snap coupling is removable.

The surgeon, with the spacer device 1 according to the present invention, can select which tooth 5 to insert in which seat 6, or in which seat 6A he/she will insert the projection 5A, so as to adjust the distance D between the stem element 2 and the head or ball element 4 or between the flat base B of the stem element 2 and the base surface 11 of the head or ball element 4.

For example, with regard to one version of the invention, the method provides for supplying a plurality of teeth 5 with open ring shape, having at least one opening C along each tooth 5 and at least one seat 6 possibly with a projection shape adapted to be inserted at the opening C of the teeth 5. Such openings C are positioned on the teeth 5 such to be parallel to each other, so as to create a channel free of projections on the surface on which such teeth are placed.

In one version, the method provides for inserting at least one projection 5A in at least one opening C and then in at least one seat 6A and rotating the two components with respect to each other, so as to connect the stem element 2 or the shank 12 to the head or ball element 4, or to its cavity 7.

The insertion of at least one projection 5A in at least one seat 6A can determine a bayonet coupling.

Also such coupling type is removable.

In particular, the projection is inserted in the opening C present in the teeth 5 and made to slide up to the desired distance from the flat base B of the stem element 2. Once such distance is reached, the head or ball element 4 is rotated so as to make the projection penetrate and slide in the space between one tooth 5 and the subsequent tooth.

In such a manner, the connection and coupling of the stem element 2 and of the head or ball element 4 of the spacer device 1 is determined, simultaneously adjusting the distance D between such two elements.

In such a manner, it is also possible that relative teeth 5 are inserted in suitable seats 6 that are sunken with respect to the surface on which they are made.

In addition, once the stem element 2 and the head or ball element 4 are assembled, the method provides for supplying a fixing material at the shank 12 and/or at the cavity 7, in a manner so as to fix the selected position. Such fixing comprises a gluing step, e.g. by means of a fixing material, such as cement, glue material, monomers or other.

In addition, in one version of the invention, the method provides for applying the filling material in the at least one recess 8. The surgeon can select which medical or pharmaceutical substance to insert in the filling material and in which of the recesses 8 to apply such substances. In such a manner, the one or more recesses 8 are filled with filling material, obtaining a smooth and continuous external surface with respect to the coupling surface 2″ of the stem element 2 and/or to the surface I of the head or ball element 4.

In a further version of the present invention, the filling material, and possibly the one or more medical or pharmaceutical substances contained therein, can already be arranged in the at least one recess 8 of the spacer device 1 by the producer of such device.

In addition, if necessary, a step can also be provided for immersing or impregnating or admixing a medical or pharmaceutical substance in the material with which the spacer device 1 is made.

Therefore, the spacer device can contain or be adapted to contain a medical or pharmaceutical substance, which can be equivalent to or different from that contained in the filling material housable in the at least one recess 8.

According to that described above, it is inferred that the spacer device according to the present invention can be personalized by the surgeon in accordance with the needs of the patient. For example, the surgeon can—if necessary—apply to the spacer device all the medical or pharmaceutical substances necessary for defeating the infection underway in the implant bone seat, by housing each in one or more recesses, in a manner so as to keep them separate from each other but present in one same device, so as to transmit each substance into the affected area or so as to transmit the various substances into the bone or articular seat, without having to mix them or apply them together.

In addition, since the opening of the at least one recess is flush with the surface of the spacer device or is flush with the external edge of the ribs N, the filling material is in turn rendered flush with such surfaces, so as to not alter the desired shape for the spacer device, i.e. that shape which allows the implant thereof.

The invention thus conceived is susceptible to numerous modifications and variations, all falling within the scope of the inventive concept.

The characteristics presented for one version or embodiment can be combined with the characteristics of another version or embodiment, without departing from the protective scope of the present invention.

In addition, all the details can be substituted by other technically equivalent elements. In practice, the materials used, as well as the contingent shapes and sizes, can be of any type in accordance with requirements, without departing from the protective scope of the following claims.

The invention claimed is:

1. A modular spacer device, implantable in a human body for treatment of an infected articular seat, comprising
    a stem element;
    coupling means; and
    a head or ball element,
    wherein said stem element is adapted to be coupled to a bone bed and said head or ball element is adapted to be inserted in an area of an articular seat of a patient,
    wherein said stem element is adapted to be removably connected by way of said coupling means to said head or ball element,
    wherein said coupling means are positioned between said stem element and said head or ball element,
    wherein said stem element comprises a distal end, an elongated body, and a portion extending from said distal end,
    wherein said distal end of said stem element comprises a shank,
    wherein said coupling means comprise a plurality of teeth and at least one projection, said plurality of teeth being arranged in parallel rows;
    wherein said at least one projection is positioned so as to be housed inside a space between two teeth to vary a distance between said head or ball element and said stem element based on anatomical characteristics of the patient and to engage said shank to said head or ball element with a bayonet engagement,
    wherein said elongated body, said portion, and said shank are made in a single piece, and
    wherein said modular spacer device comprises a fixing material, adapted to stably and permanently fix said distance of said stem element in relation to said head or ball element.

2. The modular spacer device according to claim 1, wherein said stem element comprises at least one external coupling surface, and wherein said distal end is adapted to be coupled with said head or ball element and said coupling surface is adapted to be coupled to said bone bed.

3. The modular spacer device according to claim 2, wherein said distal end comprises said shank connected to said stem element at a flat base of said stem element.

4. The modular spacer device according to claim 3, wherein said head or ball element comprises a cavity for housing said shank, and wherein said cavity comprises a lateral surface.

5. The modular spacer device according to claim 4, wherein said flat base of the stem element and a base surface of the head or ball element are placed at said distance, and wherein said coupling means are adapted to vary or adjust said distance.

6. The modular spacer device according to claim 4, wherein said shank comprises a lateral surface and has a configuration corresponding to a configuration of said cavity.

7. The modular spacer device according to claim 6, wherein said at least one projection is defined on a lateral surface of said shank.

8. The modular spacer device according to claim 4, wherein said at least one projection is defined on said lateral surface of said cavity.

9. The modular spacer device according to claim 4, wherein said shank has a cylinder shape with a height and a diameter.

10. The modular spacer device according to claim 9, wherein said cavity has a dome shape with a cylindrical base with a height and a diameter greater than, or equal to, said diameter and said height of said shank.

11. The modular spacer device according to claim 1, wherein said each of said plurality of teeth has an annular shape.

12. The modular spacer device according to claim 1, wherein each of said plurality of teeth comprises a trimming adapted to improve and render more stable or easier a coupling of said shank to said head or ball element.

13. The modular spacer device according to claim 1, wherein each of said plurality of teeth is configured as an open ring, comprising at least one opening along said open ring.

14. The modular spacer device according to claim 13, wherein said at least one opening determines a channel for insertion of said at least one projection.

15. The modular spacer device according to claim 1, wherein said each of said a plurality of teeth has a rectangular, oval, or triangular shape.

16. The modular spacer device according to claim 1, wherein one or both of said stem element or said head or ball element comprises at least one recess for housing a filling material comprising at least one pharmaceutical or medical substance.

17. A modular spacer device, implantable in a human body for treatment of an infected articular seat, comprising
a stem element;
coupling means; and
a head or ball element,
wherein said stem element is adapted to be coupled to a bone bed and said head or ball element is adapted to be inserted in an area of an articular seat of a patient,
wherein said stem element is adapted to be removably connected by way of said coupling means to said head or ball element,
wherein said coupling means are positioned between said stem element and said head or ball element,
wherein said stem element comprises a distal end, an elongated body, and a portion extending from said distal end,
wherein said distal end of said stem element comprises a shank,
wherein said coupling means comprise a plurality of teeth, at least one projection, and a plurality of seats, said plurality of teeth and said plurality of seats being arranged in parallel rows;
wherein said plurality of teeth and said plurality of seats are adapted to vary a distance between said head or ball element and said stem element based on anatomical characteristics of the patient by engaging said plurality teeth to said plurality of seats with a snap engagement, wherein said at least one projection is positioned so as to be housed inside a space between two teeth to vary the distance between said head or ball element and said stem element based on anatomical characteristics of the patient;
wherein said elongated body, said portion, and said shank are made in a single piece, and
wherein said modular spacer device comprises a fixing material, adapted to stably and permanently fix said distance of said stem element in relation to said head or ball element, and
wherein said stem element and said head or ball element are placed at said distance, and said coupling means are adapted to vary or adjust said distance.

18. The modular spacer device according to claim 17, wherein said head or ball element comprises a cavity for housing said shank.

19. The modular spacer device according to claim 18, wherein said plurality of teeth is placed on a lateral surface of said shank and said plurality of seats is defined on a lateral surface of said cavity.

20. The modular spacer device according to claim 18, wherein said plurality of teeth is placed on a lateral surface of said cavity and said plurality of seats is defined on said lateral surface of said shank.

21. The modular spacer device according to claim 17, wherein said each of said plurality of teeth has an annular shape and each of said plurality of seats is shaped as an annular cavity.

22. The modular spacer device according to claim 17, wherein each of said plurality of teeth comprises a trimming adapted to improve and render more stable or easier a coupling of said plurality of teeth to said plurality of seats.

23. The modular spacer device according to claim 17, wherein said each of said plurality of teeth is configured as an open ring, comprising at least one opening along said open ring.

24. The modular spacer device according to claim 17, wherein said each of said a plurality of teeth has a rectangular, oval, or triangular shape.

25. The modular spacer device according to claim 17, wherein one or both of said stem element or said head or ball element comprises at least one recess for housing a filling material comprising at least one pharmaceutical or medical substance.

* * * * *